(12) United States Patent
Lian et al.

(10) Patent No.: US 8,082,028 B2
(45) Date of Patent: Dec. 20, 2011

(54) DEVICE, METHOD AND COMPUTER-READABLE STORAGE MEDIUM FOR SVT AND VT CLASSIFICATION

(75) Inventors: Jie Lian, Beaverton, OR (US); Garth Garner, Tigard, OR (US); Dirk Muessig, West Linn, OR (US)

(73) Assignee: Biotronix CRM Patent AG, Baar (CH)

( * ) Notice: Subject to any disclaimer, the term of this patent is extended or adjusted under 35 U.S.C. 154(b) by 598 days.

(21) Appl. No.: 12/210,381

(22) Filed: Sep. 15, 2008

(65) Prior Publication Data
US 2009/0240300 A1 Sep. 24, 2009

Related U.S. Application Data
(60) Provisional application No. 61/037,334, filed on Mar. 18, 2008.

(51) Int. Cl.
*A61B 5/04* (2006.01)
(52) U.S. Cl. .......................... 600/515; 607/5
(58) Field of Classification Search .................. 600/515, 600/517; 607/5
See application file for complete search history.

(56) References Cited

U.S. PATENT DOCUMENTS

| | | | |
|---|---|---|---|
| 6,393,316 B1 * | 5/2002 | Gillberg et al. | 600/515 |
| 6,636,764 B1 | 10/2003 | Fain et al. | |
| 7,474,916 B2 * | 1/2009 | Gutierrez | 600/518 |
| 7,899,520 B2 * | 3/2011 | Lian et al. | 600/509 |
| 2003/0181818 A1 | 9/2003 | Kim et al. | |
| 2006/0161069 A1 | 7/2006 | Li | |
| 2006/0270937 A1 | 11/2006 | Koyrakh et al. | |

FOREIGN PATENT DOCUMENTS

| | | |
|---|---|---|
| DE | 10159296 | 6/2003 |
| EP | 1803485 | 7/2007 |
| EP | 1995685 | 11/2008 |
| WO | 2004105871 | 12/2004 |

OTHER PUBLICATIONS

European Search Report, dated Mar. 2, 2009, 8 pages.
Europea Search Report, dated Apr. 8, 2009, 10 pages.
Wilkins J. "Correlation-based pattern recognition for implantable defibrillators," Proceedings: A Conference of the American Medical Informatics Association/AMIA Annual Fall Symposium, 1996, pp. 289-293.

(Continued)

*Primary Examiner* — Brian T Gedeon
(74) *Attorney, Agent, or Firm* — ARC IP Law, PC; Joseph J. Mayo

(57) ABSTRACT

A device for classifying of supraventricular tachyarrhythmia (SVT) from ventricular tachyarrhythmia (VT) comprising means for providing a template signal and a test signal originated from an electrogram, the template signal and the test signal comprising samples, means for transforming at least the test signal resulting in a representation of the test signal where the sample values of the signal take integers, means for determining a correlation between the template signal and the test signal and means for classifying of SVT from ventricular VT based on the correlation.

19 Claims, 8 Drawing Sheets

OTHER PUBLICATIONS

Cebrian et al, "Optimization of three morphologic algorithms for arrhythmia discrimination in implantable cardioverter defibrillators," Computers in Cardiology, 2005, Lyon, France, Sep. 25-28, 2005, USA, IEEE Sep. 25, 2005, pp. 187-190.

Chang et al, "Comparison of similarity measures for clustering electrocardiogram complexes," Computers in Cardiology, 2005, Sep. 25-28, USA, IEEE, Sep. 25, 2005, pp. 759-762.

Theuns et al., "Initial clinical experience with a new arrhythmia detection algorithm in dual chamber implantable cardioverter defibrillators", Europace 2001; 3:181-186.

Sinha et al., "Clinical experience with a new detection algorithm for differentiation of supraventricular from ventricular tachycardia in a dual-chamber defibrillator", JCE 2004; 15: 646-652.

* cited by examiner

DEVICE, METHOD AND COMPUTER-READABLE STORAGE MEDIUM FOR SVT AND VT CLASSIFICATION

This application takes priority from U.S. Provisional Patent Application Ser. No. 61/037,334, filed 18 Mar. 2008, the specification of which is hereby incorporated herein by reference.

BACKGROUND OF THE INVENTION

1. Field of the Invention

The present invention generally relates to implantable cardiac devices, including pacemakers, defibrillators and cardioverters, which stimulate cardiac tissue electrically to control the patient's heart rhythm. More particularly, the present invention relates to a method and apparatus for classifying of supraventricular tachyarrhythmia (SVT) from ventricular tachyarrhythmia (VT) based on morphological analysis of the intracardiac electrogram (IEGM) recorded by the implantable cardiac devices.

2. Description of the Related Art

Implantable cardioverter-defibrillator (ICD) is a demonstrated therapy for treating life-threatening VT, including ventricular tachycardia and ventricular fibrillation. Successful ICD therapy relies on fast and accurate detection of VT. However, despite high sensitivity, one of the major limitations of the current ICD devices is the relatively low specificity for VT detection. False VT detection frequently occurs in the case of SVT, particular in the case of 1:1 AV association. Consequently, this low specificity often results in inappropriate ICD shocks delivered for SVT, causing patient's discomfort, negatively affecting their quality of life, and reducing device longevity because of unnecessary current drain.

Conventionally, the VT detection algorithm in the ICDs is based on cardiac inter-beat or RR interval analysis. Different VT zones are programmed based on predefined thresholds of RR intervals or ventricular rates. Because SVT frequently results in short RR intervals or high ventricular rates that also fall in the VT zone, enhancement of the VT detection algorithm was made by including additional criteria such as sudden onset and stability.

For dual-chamber ICDs, the discrimination of SVT from VT can be substantially enhanced by the addition of atrial sensing capability. Many types of SVT rhythms, such as atrial flutter and atrial fibrillation, can be easily distinguished from the VT by the evidence of AV dissociation. However, the challenge to discriminate SVT from VT in the presence of 1:1 AV relationship, such as during sinus tachycardia or AV nodal reentrant tachycardia, still remains.

Morphological analysis has also been used to facilitate the SVT-VT classification. Usually, a template IEGM of conducted baseline rhythm is recorded and maintained. During fast ventricular activation, the rhythm is classified as SVT if the IEGM morphology is similar to the template waveform, whereas it is classified as VT if the IEGM morphology is distinctly different from the template waveform. All morphology-based SVT-VT classification algorithms require proper alignment of the template waveform and the test IEGM.

One morphology analysis method is based on correlation analysis. However, the calculation of conventional correlation coefficient (CC) between two vectors requires extensive floating-point operation, which renders it not feasible for implementation in the low-power devices or systems. As a compromise, an algorithm may only select a small number of samples from the signal (for example 8) to calculate an alternative index termed feature correlation coefficient (FCC). Despite this simplification, the computation load is still high due to the floating-point operation. Also, the waveform morphology is unlikely to be fully characterized by the limited 8 samples, thus FCC may not accurately quantify the similarity between two waveforms. Furthermore, similar to CC, the FCC is less sensitive to the amplitude discrepancy between the signals. For example, the FCC between two signals X and $Y=\rho \cdot X$, where $\rho$ is a constant scaling factor, is always 1, despite the fact that the amplitude of Y can be significantly different than that of X. Finally, the FCC between two signals is affected by each sample amplitude of each signal, thus is sensitive to additive noise such as impulse noise and continuous random noise.

Another morphology analysis method is based on metrics that are derived from the signals. The metric used in this algorithm is the peak area of the IEGM waveform, while other metrics (weight, height, zero-crossing, etc.) may also be used. The algorithm measures the difference between the corresponding (normalized) peak areas of the test and template IEGM waveforms. Then a morphology score is generated based on the peak area difference to indicate the similarity between test and template IEGM signals. However, the metric (peak area) derived from the signal is affected by many factors, such that waveforms of different morphologies can have the same metric value. In principle, the waveform morphology is unlikely to be fully characterized by a single or multiple metrics, thus the derived morphology score may not accurately quantify the similarity between two waveforms. Moreover, such an algorithm is known to be very sensitive to the waveform alignment errors.

Wavelets, especially modified Haar wavelets, have also been used to facilitate discrimination between SVT and VT. In particular, the modified Haar wavelets were used to decompose the IEGM signal into wavelet coefficients. To compare the morphology between a test IEGM and the template waveform, their respective wavelet coefficients are compared. If the match percentage between their wavelet coefficients is greater than a threshold (e.g., 70%), then the test IEGM is considered similar to the template waveform, indicating a conducted beat. Otherwise, the test IEGM is thought to have different morphology than the template waveform, suggesting ventricular origin of the beat. However, because in practice, only limited number of wavelet coefficients are retained to represent the IEGM waveform, some subtle morphological information may be lost through the wavelet transform. As a result, the match percentage between wavelet coefficients may not accurately reflect the morphological similarity between two signals.

In view of above, there is a need to provide a novel method to accurately, efficiently, and robustly measure the morphological similarity between an IEGM signal and a template waveform, to facilitate discrimination between SVT and VT.

BRIEF SUMMARY OF THE INVENTION

It is an object of the invention to provide a device, for example an implantable cardiac device, such as a pacemaker, a defibrillator or a cardioverter, for classifying of supraventricular tachyarrhythmia (SVT) from ventricular tachyarrhythmia (VT). The device comprises means for providing a template signal and a test signal originated from an electrogram. The template signal and the test signal comprising samples. The device comprises further means for transforming at least the test signal resulting in a representation of the test signal where the sample values of the signal take integers.

The device comprises further means for determining a correlation between the template signal and the test signal, and means for classifying of SVT from ventricular VT based on the correlation.

The electrogram may be an intracardiac electrogram (IEGM), a surface electrocardiogram (ECG) or a subcutaneous electrogram.

The invention provides a device which further comprises means for averaging a plurality of cycles of signals to obtain the template signal. Especially cycles of conducted ventricular IEGM signals may be used.

The invention provides a device which further comprises means for updating the template periodically or continuously after an initial template setup.

The invention provides a device which further comprises means for aligning the signals based on at least one predefined fiducial point.

A further object of the invention is providing a device which further comprises means for associating the template signal with at least two subspaces of the template signal space and means for transforming at least one of the template signal and the test signal with respect to the subspaces.

In an embodiment the means for associating the template signal with at least two subspaces comprises means for defining a first subspace comprising values which differ from the template signal values at the most by a predefined first value, and means for defining a second subspace comprising values which differ from the template signal values at the least by the predefined first value.

In an other embodiment the means for associating the template signal with at least two subspaces comprises means for associating the template signal with three subspaces, and means for defining a first subspace comprising values which differ from the template signal values at the most by a predefined first value, means for defining a second subspace comprising values which differ from the template signal values at the least by the predefined first value and at the most by a predefined second value, and means for defining a third subspace comprising values which differ from the template signal values at the least by the predefined second value.

According to another aspect of the invention the device further comprising means for generating threshold vectors bounding the subspaces, where the threshold vectors are generated by increasing or decreasing the sample values of the template signal by a predefined value.

According to yet another aspect of the invention the means for transforming comprises means for setting a sample value of the transformed signal to a first, second or third integer if the corresponding sample value of the signal belongs to the first, second or third subspace. In a special embodiment the first integer is set to 1, the second integer is set to 0 and the third integer is set to −1.

In a further embodiment of the invention the device comprises means for determining a correlation using at least the transformed test signal.

In yet a further embodiment of the invention the device comprises means for determining a correlation using only the transformed test signal.

In another embodiment the means for determining a correlation comprises means for determining an Adapted Signed Correlation Index (ASCI) as the sum of the sample values of the transformed test signal or by dividing the sum of the sample values of the transformed test signal by the number of samples.

According to an aspect of the invention the means for classifying comprises means for classifying a ventricular IEGM as being of ventricular origin if the correlation is below a predefined threshold, or as being of supraventricular origin otherwise.

According to another aspect of the invention the means for classifying comprises means for performing SVT-VT classification by a combination of determining the correlation between the template signal and the test signal and RR interval analysis.

In an embodiment the means for classifying further comprises means for incrementing a VT sample counter by 1 for a ventricular cycle that falls in the VT/VF zone if and only if the correlation value between the ventricular cycle and the template signal is below a predefined threshold.

According to yet an other aspect of the invention the means for classifying comprises means for performing SVT-VT classification by a combination of determining the correlation between the template signal and the test signal and SVT-VT classification algorithm that involves both atrial and ventricular rate and rhythm analysis.

According to yet another aspect of the invention the template signal is an atrial IEGM waveform and the means for classifying comprises means for determining the correlation between an atrial test IEGM signal with the atrial IEGM waveform in case a SVT or VT with 1:1 relationship is detected for distinguishing an intrinsic atrial event from a retrograde conducted atrial event.

It is further an object of the invention to provide a method for classifying of supraventricular tachyarrhythmia (SVT) from ventricular tachyarrhythmia (VT) using signals provided by an electrogram comprising the steps of:

providing a template signal and a test signal, the template signal and the test signal comprising samples;

transforming at least the test signal resulting in a representation of the test signal where the sample values of the signal take integers;

determining a correlation between the template signal and the test signal; and classifying of SVT from ventricular VT based on the correlation.

According to an aspect of the invention the signals are provided by an intracardiac electrogram (IEGM), a surface electrocardiogram (ECG) or a subcutaneous electrogram.

In an embodiment of the invention the template signal is obtained by averaging a plurality of cycles of signals, where cycles of conducted ventricular IEGM signals may be used.

In an embodiment of the invention after an initial template setup the template is updated periodically or continuously.

In another embodiment of the invention the signals are aligned based on at least one predefined fiducial point.

According to another aspect of the invention the method for classifying of SVT from VT comprises the further steps of:

associating the template signal with at least two subspaces of the template signal space and transforming at least one of the template signal and the test signal with respect to the subspaces.

In an embodiment of the invention the at least two subspaces are defined by a first subspace comprising values which differ from the template signal values at the most by a predefined first value, and a second subspace comprising values which differ from the template signal values at the least by the predefined first value.

In another embodiment of the invention the template signal is associated with three subspaces and the three subspaces are defined by a first subspace comprising values which differ from the template signal values at the most by a predefined first value, a second subspace comprising values which differ from the template signal values at the least by the predefined first value and at the most by a predefined second value, and a third subspace comprising values which differ from the template signal values at the least by the predefined second value.

According to an aspect of the invention the subspaces are bounded by threshold vectors.

In an embodiment of the invention the threshold vectors are obtained by increasing or decreasing the sample values of the template signal by a predefined value.

In an embodiment of the invention transforming the signals comprises assigning a first, second or third integer to a sample of the transformed signal if the corresponding sample of the signal belongs to the first, second or third subspace. The first integer may be set to 1, the second integer may be set to 0 and the third integer may be set to −1.

According to an aspect of the invention determination of the correlation is performed using the transformed test signals.

According to another aspect of the invention determination of the correlation is performed using only the transformed test signal.

In an embodiment of the invention for determining a correlation a ASCI (Adapted Signed Correlation Index) is determined as the sum of the sample values of the transformed test signal or by dividing the sum of the sample values of the transformed test signal by the number of samples.

According to an aspect of the invention a ventricular IEGM is classified as being of ventricular origin if the correlation is below a predefined threshold, or as being of supraventricular origin otherwise.

According to another aspect of the invention SVT-VT classification is performed by a combination of determining the correlation between the template signal and the test signal and RR interval analysis.

In an embodiment for a ventricular cycle that falls in the VT/VF zone a VT sample counter is increment by 1 if and only if the correlation value between the test and the template signal is below a predefined threshold.

According to yet an other aspect of the invention SVT-VT classification is performed by a combination of determining the correlation between the template signal and the test signal and SVT-VT classification algorithm that involves both atrial and ventricular rate and rhythm analysis.

According to a further aspect of the invention the template signal is an atrial IEGM waveform and determining the correlation between an atrial test IEGM signal with the atrial IEGM waveform in case a SVT or VT with 1:1 relationship is detected for distinguishing an intrinsic atrial event from a retrograde conducted atrial event.

It is further an object of the invention to provide a computer-readable storage medium storing program code for causing a data processing device to perform a method for classifying of supraventricular tachyarrhythmia (SVT) from ventricular tachyarrhythmia (VT) using signals provided by an electrogram, the method comprising the steps of:

providing a template signal and a test signal, the template signal and the test signal comprising samples;

transforming at least the test signal resulting in a representation of the test signal where the sample values of the signal take integers;

determining a correlation between the template signal and the test signal; and classifying of SVT from ventricular VT based on the correlation.

According to this invention, the ASCI is used to quantify the morphological similarity between an IEGM signal and a template waveform. All valid sample pairs are included in the calculation of ASCI, thus complete waveform morphology information of the two signals is retained (i.e., no loss of morphological information due to feature extraction). The calculation of ASCI is computationally efficient because no floating-point operation is necessary. Furthermore, calculation of ASCI is robust against measurement noise and minor alignment error of the signals.

According to this invention, the template waveform is created by averaging multiple cycles of conducted ventricular IEGM, which is aligned with predefined fiducial point. Preferably, the template waveform is created at high atrial rate (sinus rhythm or atrial pacing) but below the VT detection rate. The template waveform is also preferably updated periodically or dynamically to reflect the gradual change of the conducted IEGM morphology.

In a preferred embodiment, upon detection of high ventricular rate, the ASCI-based morphological analysis is activated to enhance the existing SVT-VT classification algorithm. For a short ventricular cycle, the ASCI between this cycle's IEGM and the template waveform is calculated. If the ASCI is greater than a predefined threshold, it indicates the test IEGM has similar morphology as the template waveform, suggesting this is a conducted beat. Otherwise, it indicates the test IEGM has different morphology than the template waveform, suggesting the ventricular origin of the beat.

In this invention, although the IEGM signals are used to illustrate the concept of ASCI-based morphology analysis for SVT and VT classification, it should be understood that the same method could be applied to SVT and VT classification based on surface ECG or subcutaneous electrogram signals.

The details of the invention can be understood from the following drawings and the corresponding text descriptions.

DETAILED DESCRIPTION OF THE INVENTION

Construction of Template Waveform

For the purpose of SVT and VT classification, the template waveform is constructed from the electrogram signal that corresponds to antegrade conducted ventricular beat. For implantable cardiac devices, the template waveform can be constructed from the ventricular IEGM corresponding to ventricular sense (VS) event that is associated with preceding atrial sense (AS) or atrial pace (AP) event.

Figure 1:
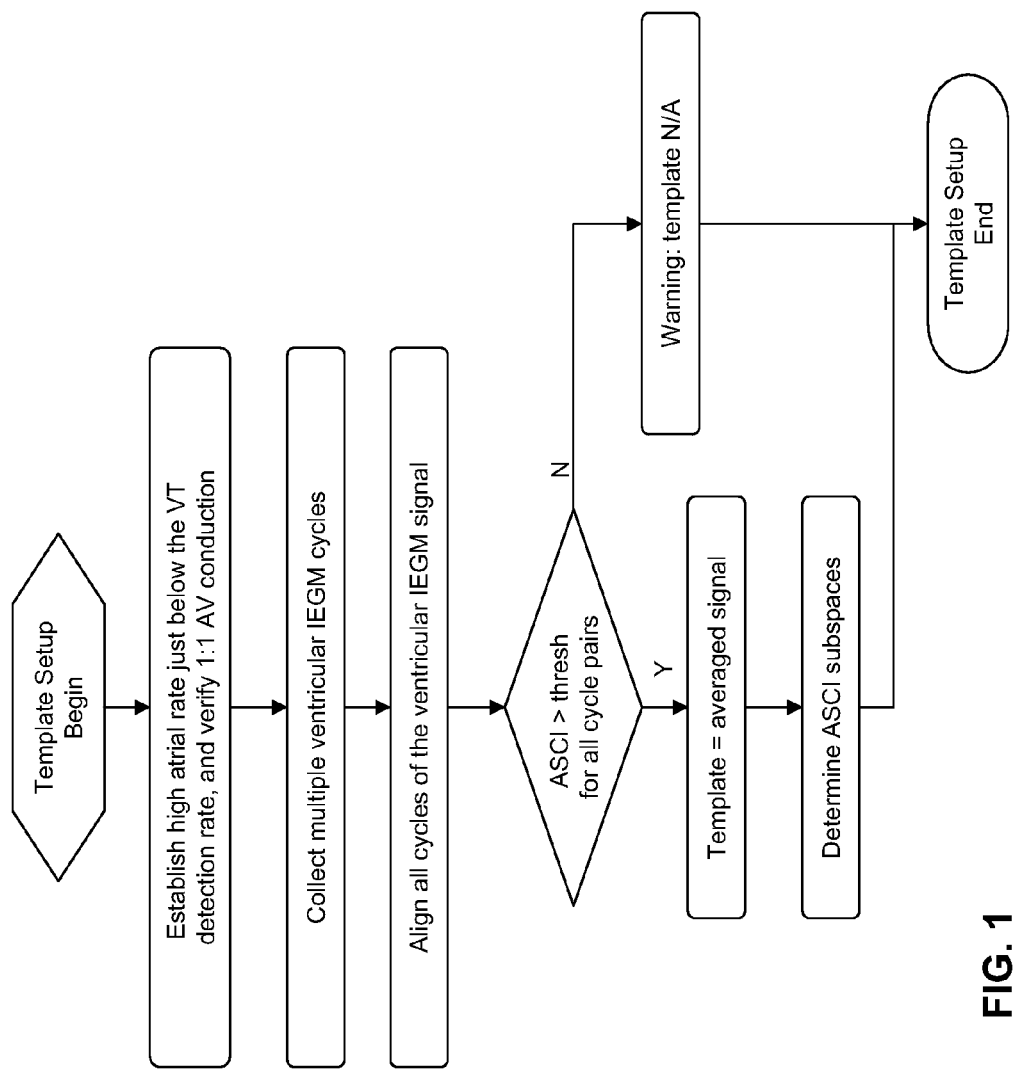
FIG. 1 is a high-level flowchart diagram that illustrates the steps involved in automatic setup of the conducted ventricular IEGM template in an ICD.

FIG. 1 shows a high-level flowchart diagram that illustrates the steps involved in automatic setup of the conducted ventricular IEGM template in an ICD. Preferably, the template waveform is created at an atrial rate that is higher than a predefined 'template rate', but below the programmed VT detection rate. In a typical example, the 'template rate' is defined as 20 ppm below the programmed VT detection rate. The high atrial rate can be achieved at elevated sinus rhythm, for example, during stress test, or by means of high rate atrial pacing. It is also required that 1:1 AV conduction is maintained during the template setup phase.

Then the ICD collects multiple cycles of the conducted ventricular IEGM signal, which are then aligned based on predefined fiducial point, for example, the positive or negative peak, the maximum slope, the threshold crossing point, etc., as known in the art. For each cycle, the IEGM segment in a fixed window relative to the fiducial point is selected for creating the template signal. In a typical embodiment, the fiducial point is chosen as the dominant peak (positive or negative) of the ventricular IEGM, and the IEGM window spans from 50 ms before the fiducial point to 100 ms after the fiducial point.

Still refer to FIG. 1. According to this invention, for each pair of the aligned and windowed ventricular IEGM signals, their morphological similarity is quantified by an Adaptive Signed Correlation Index (ASCI), which will be described in details in the following sections. If for any given cycle pair, the calculated ASCI is lower than a predefined threshold value, then the collected ventricular IEGM signals are considered not stable. A warning is generated by the ICD indicating the template signal is not available at the moment, and the template setup may be retried at a later time. On the other hand, if for all cycle pairs, the calculated ASCI is greater than the predefined threshold value (e.g., 0.8), then all collected ventricular IEGM cycles are considered similar, and the conducted ventricular IEGM template is created by averaging all these aligned IEGM cycles.

As discussed in more details later, the ASCI is calculated based on the definition of three subspaces which are dependent on the template signal. Thus upon creation of the conducted ventricular IEGM template, the ICD further determines the three subspaces as discussed thereinafter. Note that during the initial template setup phase when template waveform has not been available yet, to calculate the ASCI between a pair of IEGM cycles, any one of the two IEGM signals can be initialized as the tentative template signal. Based on this tentative template signal, the three subspaces can be defined, and the similarity between these two signals can be quantified by ASCI. As discussed above, only when all pairs of the collected IEGM cycles result in higher than predefined threshold ASCI values, then these cycles are considered to have similar morphology, and the true template waveform can be created.

Figure 2:
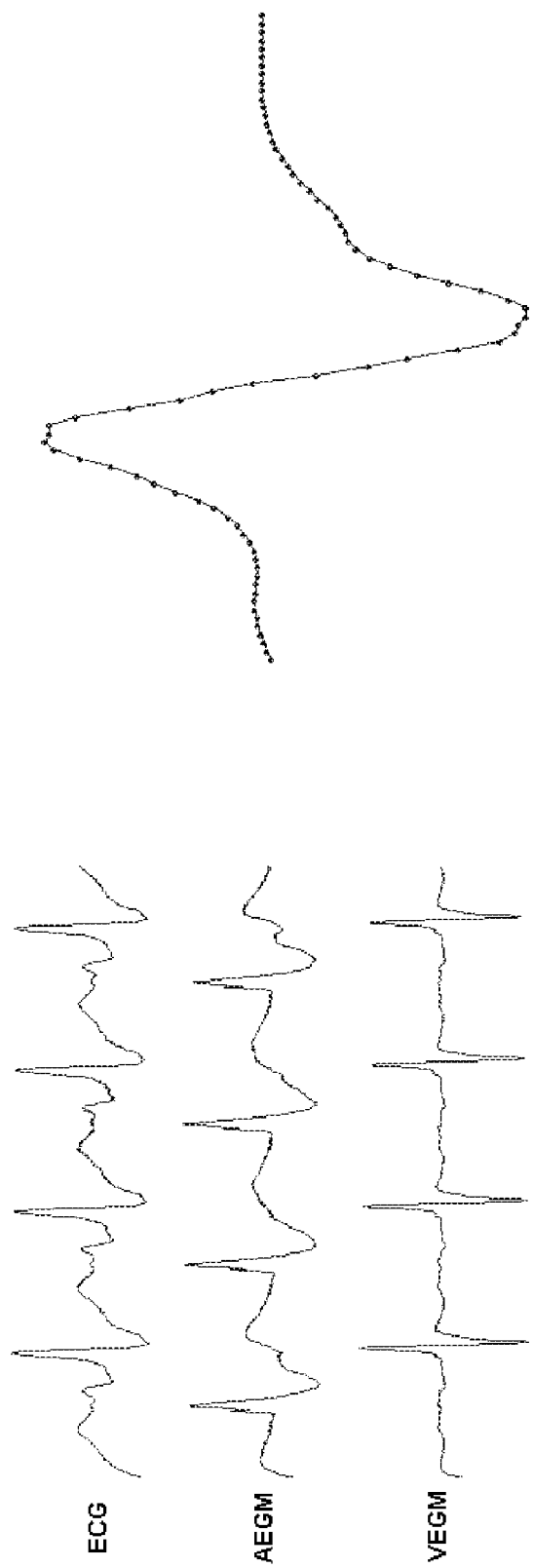
FIG. 2 shows an example of template setup for conducted ventricular IEGM signals.

FIG. 2 shows a particular example of template setup for conducted ventricular IEGM signals. In this example, the surface ECG, the atrial IEGM, and the ventricular IEGM are shown (left) for four cardiac cycles in sinus rhythm. Each intrinsic atrial depolarization is followed by a conducted ventricular depolarization. The ventricular IEGM morphology is consistent among the four cycles. The positive peak of the ventricular IEGM is chosen as the fiducial point, and the window size is set from 50 ms before the positive peak to 100 ms after the positive peak. Then the four cycles of ventricular IEGM are averaged to create the conducted ventricular IEGM template waveform (right).

Update of Template Waveform

According to this invention, after the initial template setup, the conducted ventricular IEGM template is preferably updated periodically or continuously to reflect the dynamic change of the conducted IEGM morphology. This template running update feature is important because the conducted ventricular IEGM waveform may gradually change over time due to different factors such as heart rate variation, circadian pattern, changes of medication, changes of electrode-tissue interface, etc.

Figure 3:
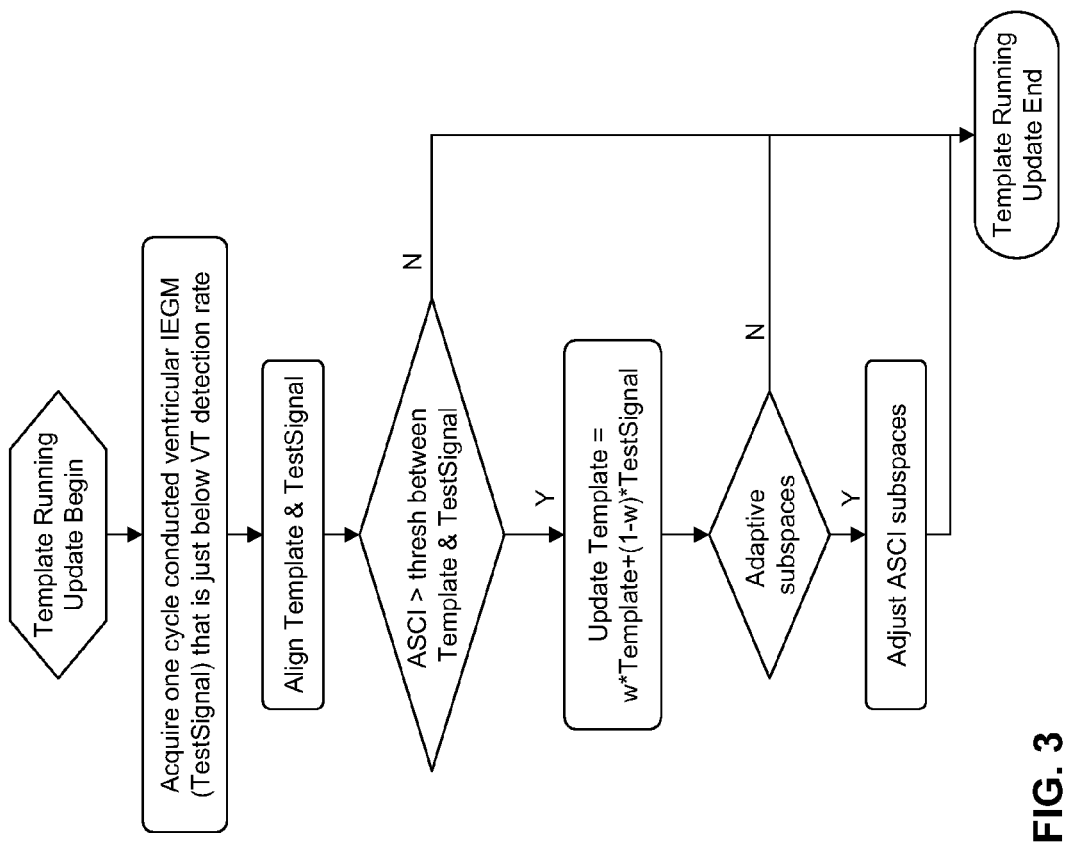
FIG. 3 shows a high-level flowchart that illustrates the steps involved in running update of the conducted ventricular IEGM template.

FIG. 3 shows a high-level flowchart that illustrates the steps involved in running update of the conducted ventricular IEGM template. Preferably, the template running update is activated if and only if the atrial rate (sensed or paced) is higher than the predefined 'template rate' but below the programmed VT detection rate. Upon activation of the template running update, the ICD acquires one cycle of conducted ventricular IEGM (i.e., preceded by an AS or AP event) as the test signal, which is aligned with the template signal based on predefined fiducial point as discussed above. Then the ICD calculates the ASCI between the template signal and the acquired test signal. If the ASCI is lower than a predefined threshold (e.g., 0.8), then the test signal is considered different than the template signal, and no template update is performed for this test cycle. On the other hand, if the calculated ASCI is greater than the predefined threshold (e.g., 0.8), then the test signal is considered similar to the template signal, and the template signal is updated by taking the weighted average of the original template signal and the newly acquired test signal. In an exemplary embodiment, the new template is the sum of the old template signal scaled by 255/256, and the newly acquired test signal scaled by 1/256. By this means, it ensures the stability of the template waveform by retaining 255/256 of the old template signal, whereas it incorporates 1/256 of the test signal to factor in any gradual change of the conducted ventricular IEGM morphology. As discussed in more details later, the ASCI is calculated based on the definition of three subspaces which are dependent on the template signal. Thus the ICD can further adjust the three subspaces based on newly updated template signal, if the adaptive subspace feature is enabled.

Signal Alignment

One prerequisite for any morphology-based SVT-VT classification algorithms is that the test signal must be properly aligned with the template signal. Morphological analysis based on misaligned signals may yield misleading results. As discussed above, the common practice for signal alignment is based on a predefined fiducial point, such as the positive peak, the negative peak, etc. However, in some cases, the signal alignment based on a single fiducial point is not reliable.

Figure 4:
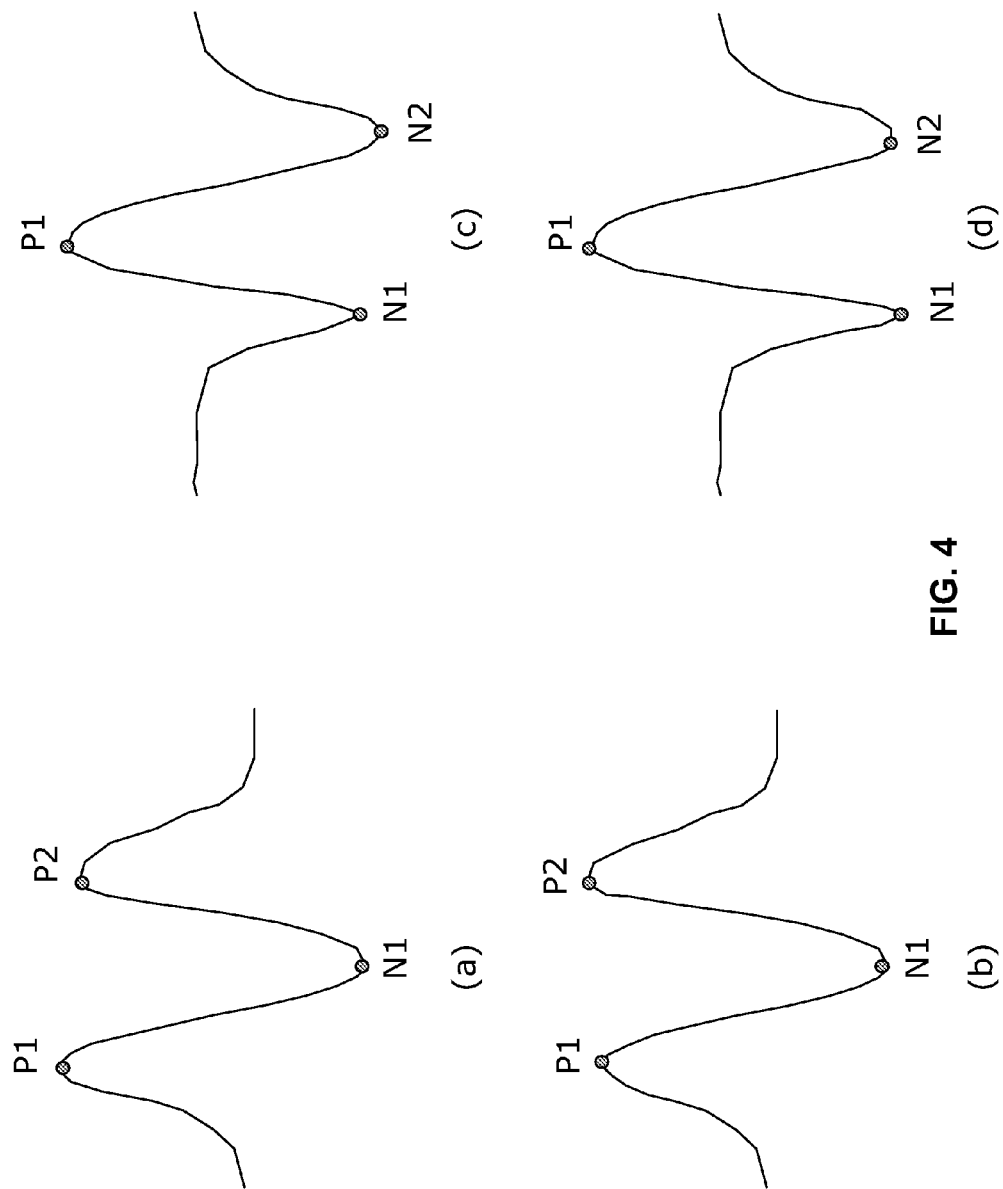
FIG. 4 illustrates the concept of signal alignment using multiple fiducial points.

FIG. 4 shows some examples. Panels (a) and (b) show two signal complexes that have similar morphology. Both signal complexes can be characterized by two positive peaks (P1, P2) that have similar amplitude and one negative peak (N1). If the dominant positive peak is chosen as the fiducial point, then the fiducial point will be P1 for the signal complex shown in panel (a) but P2 for the signal complex shown in panel (b). Similarly, panels (c) and (d) show another pair of signal complexes that have similar morphology. Both signal complexes can be characterized by two negative peaks (N1, N2) that have similar amplitude and one positive peak (P1). If the dominant negative peak is chosen as the fiducial point, then the fiducial point will be N2 for the signal complex shown in panel (c) but N1 for the signal complex shown in panel (d).

According to this invention, multiple fiducial points are defined for signal alignment in adjunction with ASCI-based morphological analysis. Specifically, for a given template signal representing conducted ventricular IEGM, multiple fiducial points (if available) are defined in a sequential order, that is, 1st fiducial point, 2nd fiducial point, 3rd fiducial point, etc. Similar fiducial points (if available) are also identified for a test ventricular IEGM signal. For example, for the signals shown in panels (a) and (b) of FIG. 4, the fiducial points can be defined in the following order: dominant positive peak (1st fiducial point; P1 in (a) and P2 in (b)), dominant negative peak (2nd fiducial point; N1 in both (a) and (b)), secondary positive peak (3rd fiducial point; P2 in (a) and P1 in (b)). Similarly, for the signals shown in panels (c) and (d) of FIG. 4, the fiducial points can be defined in the following order: dominant positive peak (1st fiducial point; P1 in both (c) and (d)), dominant negative peak (2nd fiducial point; N2 in (c) and N1 in (d)), secondary negative peak (3rd fiducial point; N1 in (c) and N2 in (d)).

To compare the morphology of the test signal and the template signal, the two signals are first aligned with the 1st fiducial point, and their ASCI value is calculated. If the resulting ASCI value is higher than a predefined threshold (e.g., 0.8), then it indicates the two signals have similar morphology (as described in details below). The signal alignment is considered valid, and no further calculation is needed. On the other hand, if the resulting ASCI value is lower than the predefined threshold (e.g., 0.8), then it indicates the two signals have different morphology (as described in details below). Then the signals are re-aligned with the 2nd fiducial point (if available for both signals), and their ASCI value is re-calculated. If the re-calculated ASCI value is higher than the predefined threshold (e.g., 0.8), then it indicates misalignment for the 1st fiducial point, but the alignment based on the 2nd fiducial point is valid. The signals are considered to have similar morphology and no further calculation is needed. Similar test can be performed for the 3rd fiducial point (if available for both signals) if the ASCI value obtained for the 2nd fiducial point is still lower than the predefined threshold (e.g., 0.8). No further test is needed if a fiducial point is only available for one signal but not the other signal. If all ASCI values are below the predefined threshold (e.g., 0.8), no matter which fiducial point is chosen, then it is determined that the test signal and the template signal have different morphology.

According to the experience of the present inventors, using two fiducial points (e.g., dominant positive peak and dominant negative peak) for signal alignment can effectively solve most of the signal misalignment problems caused by using a single fiducial point.

Definition of Adaptive Subspaces

Figure 5:
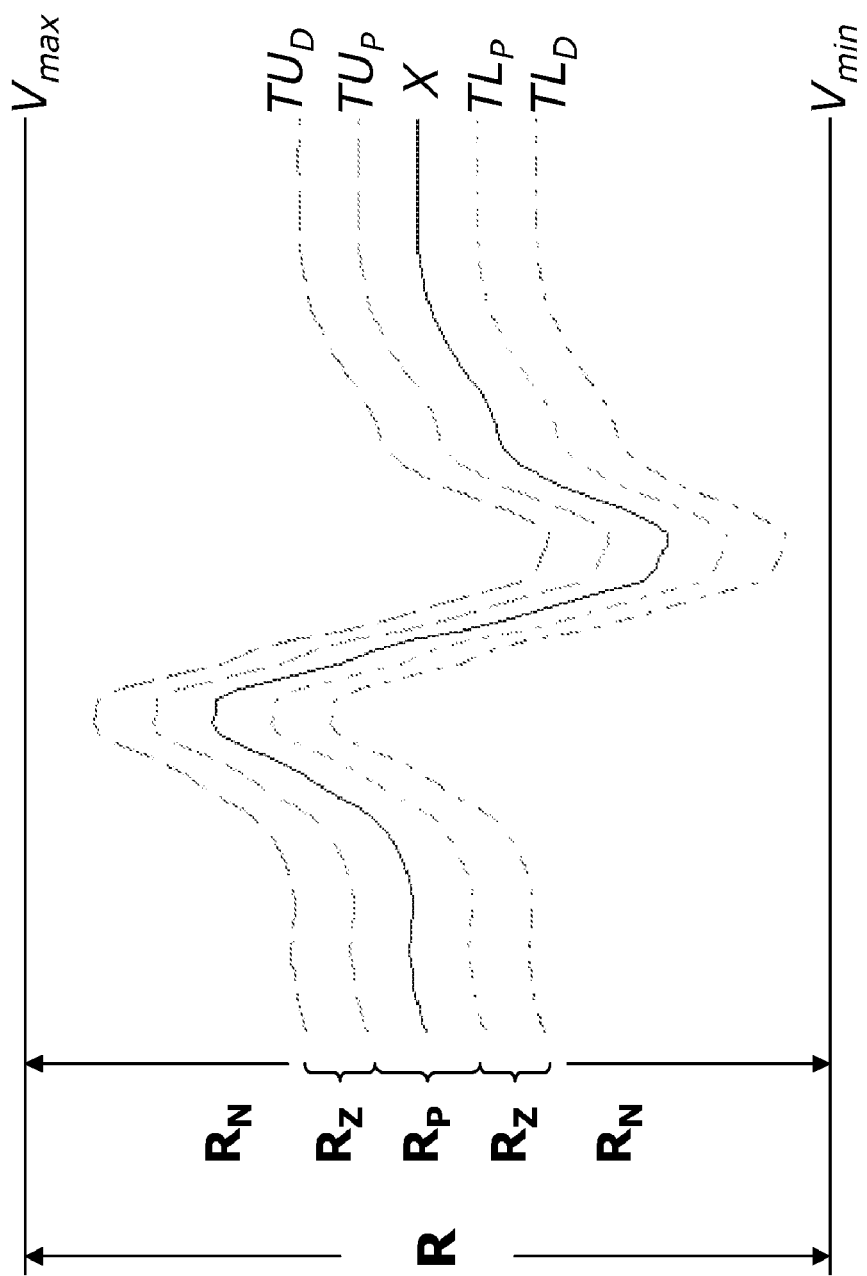
FIG. 5 illustrates the concept of three subspaces defined by four threshold vectors that are adaptive to the template signal.

Refer to FIG. 5. Let R denote the ventricular IEGM signal space that spans from $V_{min}$ to $V_{max}$, where $V_{min}$ is the minimum amplitude and $V_{max}$ is the maximum amplitude that could be measured by the ventricular sensing channel. Divide R into three subspaces $R_P$, $R_Z$, and $R_N$ such that $R = R_P \cup R_Z \cup R_N$ and $R_P \cap R_Z = R_P \cap R_N = R_Z \cap R_N = \emptyset$, where $\cup$ is the union operator, $\cap$ is the intersection operator, and $\emptyset$ represents the null space. That is, the three subspaces are non-overlapping yet all together they span the whole signal space. For convenient purpose, in the following descriptions, we term $R_P$ as the positive subspace, $R_Z$ as the zero subspace, and $R_N$ as the negative subspace.

Still refer to FIG. 5. According to this invention, all three subspaces ($R_P$, $R_Z$, $R_N$) are adaptive to the template signal representing conducted ventricular IEGM morphology. In a preferred embodiment, four threshold vectors $TL_D$, $TL_P$, $TU_P$, $TU_D$ are defined from the template signal X. Denote $X=[x(1), x(2), \ldots, x(L)]$, where L is the number of samples in signal X. Further denote $TL_P=[tlp(1), tlp(2), \ldots, tlp(L)]$ as the proximal lower threshold vector, $TL_D=[tld(1), tld(2), \ldots, tld(L)]$ as the distal lower threshold vector, $TU_P=[tup(1), tup(2), \ldots, tup(L)]$ as the proximal upper threshold vector, and $TU_D=[tud(1), tud(2), \ldots, tud(L)]$ as the distal upper threshold vector. These threshold vectors are defined such that $TL_D \leq TL_P \leq X \leq TU_P \leq TU_D$, or specifically, $tld(i) \leq tlp(i) \leq x(i) \leq tup(i) \leq tud(i)$, for $1 \leq i \leq L$. The positive subspace $R_P$ is defined as the region bounded by $TL_P$ and $TU_P$, the negative subspace $R_N$ is defined as the region above $TU_D$ or below $TL_D$, and the zero subspace $R_Z$ is defined as the region bounded between $TU_P$ and $TU_D$, and that between $TL_D$ and $TL_P$. Obviously, a sample in $R_P$ is proximal to the template, a sample in $R_N$ is distal to the template, and a sample in $R_Z$ is at intermediate distance to the template.

According to an exemplary embodiment of the present invention, the four threshold vectors are defined from the template signal according to the following equations:

$$TU_P = X + \alpha \cdot \max(abs(X))$$

$$TL_P = X - \alpha \cdot \max(abs(X))$$

$$TU_D = X + \beta \cdot \max(abs(X))$$

$$TL_D = X - \beta \cdot \max(abs(X))$$

Here, max(abs(X)) is the peak absolute amplitude of the template signal, $\alpha$ and $\beta$ are programmable scaling coefficients that satisfy $0 < \alpha < \beta$. In a typical example, $\alpha = 0.25$ and $\beta = 0.5$, and the resulting threshold vectors are symmetric around the template signal.

Obviously, there are numerous other means to define the four threshold vectors so that they are adaptive to the template signal X, for example, either based on sample-by-sample amplitude of X, or based on specific features of X, such as its maximum, minimum, max absolute, mean, median, etc., or their combinations. Also, the upper threshold vectors and the lower threshold vectors can be symmetric or asymmetric around the template signal.

As illustrated in FIG. 1, after automatic setup of the conducted ventricular IEGM template, the three subspaces can be defined from four threshold vectors that are adaptive to the template signal by means of the method described above. Similarly, during the template running update as illustrated in FIG. 3, after the template signal is updated by taking the weighted average of the old template signal and the new test signal, the three subspaces can be adjusted by redefining the threshold vectors based on the new template.

Signal Trichotomization

To calculate the ASCI between two IEGM signals, both signals are first trichotomized based on three subspaces that are adaptive to the defined template signal.

Denote S as the three-value set $\{-1, 0, 1\}$. Assume $X=[x(1), x(2), \ldots, x(L)]$ is a ventricular IEGM signal, that is, $x(i) \in R$ for $i=1, 2, \ldots L$, where L is the number of samples in signal X. Trichotomization of signal X is an operation that maps the signal from R space to S space. Specifically, denote $TX=[tx(1), tx(2), \ldots, tx(L)]$ as the trichotomized signal of X, where $tx(i) \in S$ for $i=1, 2, \ldots L$. Then the trichotomization is formulated as, for $$tx(i) = \begin{cases} 1 & \text{if } x(i) \in R_P \\ 0 & \text{if } x(i) \in R_Z \\ -1 & \text{if } x(i) \in R_N \end{cases}$$

In other words, signal X is trichotomized to TX by converting all its data samples to values selected from $\{-1, 0, 1\}$, based on which subspace each data sample belongs to.

In a typical embodiment, signal X is the template signal representing conducted ventricular IEGM morphology, and ASCI(X,Y) measures the similarity between a test ventricular IEGM signal Y and the template signal X. For the template signal X, all elements of its trichotomized signal TX are 1 because all samples of X are within the positive subspace $R_P$. For another signal Y, its trichotomized signal TY will have more 1s if more samples of Y are close to the corresponding samples of X, i.e., Y is similar to X. As Y gradually deviates from X, its trichotomized signal TY has less 1s, more 0s, and eventually more –1s.

Calculation of ASCI

Assume $X=[x(1), x(2), \ldots, x(L)]$ and $Y=[y(1), y(2), \ldots, y(L)]$ are two signals in R, and each has L samples. Given defined subspaces $R_P$, $R_Z$, and $R_N$ (which are adaptive to the template signal), X is trichotomized to $TX=[tx(1), tx(2), \ldots, tx(L)]$, and Y is trichotomized to $TY=[ty(1), ty(2), \ldots, ty(L)]$. The ASCI between X and Y, or ASCI(X,Y), which measures the similarity between X and Y, is defined by the following formula:

$$ASCI(X, Y) = \frac{TX \circ TY}{\sqrt{TX \circ TX} \cdot \sqrt{TY \circ TY}}$$

Here, the symbol ∘ denotes the signed correlation product (SCP) of two trichotomized vectors, and is defined by the following formula:

$$TX \circ TY = \sum_{i=1}^{L} tx(i) \otimes ty(i)$$

Here, the symbol ⊗ denotes the signed correlation product (SCP) between two trichotomized scalars, and is defined by the following formula:

$$tx(i) \otimes ty(i) = \begin{cases} 1 & \text{if } tx(i) = ty(i) \\ -1 & \text{if } tx(i) \cdot ty(i) = -1 \\ 0 & \text{otherwise} \end{cases}$$

Accordingly, if tx(i)=ty(i), their SCP is 1. In this case, the sample pair x(i) and y(i) are considered concordant, meaning that they are in the same subspace. Specifically, both are in the positive subspace if tx(i)=ty(i)=1; or both are in the negative subspace if tx(i)=ty(i)=–1; or both are in the zero subspace if tx(i)=ty(i)=0.

On the other hand, if tx(i)·ty(i)=–1, their SCP is –1. In this case, the sample pair x(i) and y(i) are considered discordant. Specifically, it occurs when tx(i)=1 and ty(i)=–1, or tx(i)=–1 and ty(i)=1. In both cases, one sample is in the positive subspace whereas the other sample is in the negative subspace.

Otherwise, the case must be either tx(i)=0 and ty(i)≠0, or tx(i)≠0 and ty(i)=0, and their SCP is 0. In this case, the sample pair x(i) and y(i) are considered neither concordant, nor discordant. Specifically, one sample is within the zero subspace, and the other sample is either in the positive subspace or in the negative subspace.

According to the above definition, the SCP of two trichotomized vectors (TX∘TY) is the sum of the SCP of all sample pairs tx(i)⊗ty(i), for i=1 . . . L. Therefore, the SCP of two trichotomized signals will be increased by each pair of concordant samples (+1), decreased by each pair of discordant samples (–1), and not affected otherwise (neither concordant nor discordant sample pair).

For two identical signals, all corresponding sample pairs are concordant. Therefore, for above defined TX and TY, it is evident that TX∘TX=L and TY∘TY=L. Consequently, the formula for calculating ASCI(X,Y) defined above can be simplified to:

$$ASCI(X, Y) = \frac{TX \circ TY}{L}$$

As discussed above, in a typical embodiment, signal X is the template signal representing conducted ventricular IEGM morphology, and all elements of its trichotomized signal TX are 1 because all samples of X are within the positive subspace. Therefore, the formula for calculating ASCI(X,Y) defined above can be further simplified to:

$$ASCI(X, Y) = \frac{\sum_{i=1}^{L} ty(i)}{L}$$

In other words, the ASCI(X,Y) can be simply calculated as the accumulative sum of all trichotomized samples of test signal Y normalized by the number of samples.

Properties of ASCI

Figure 6:
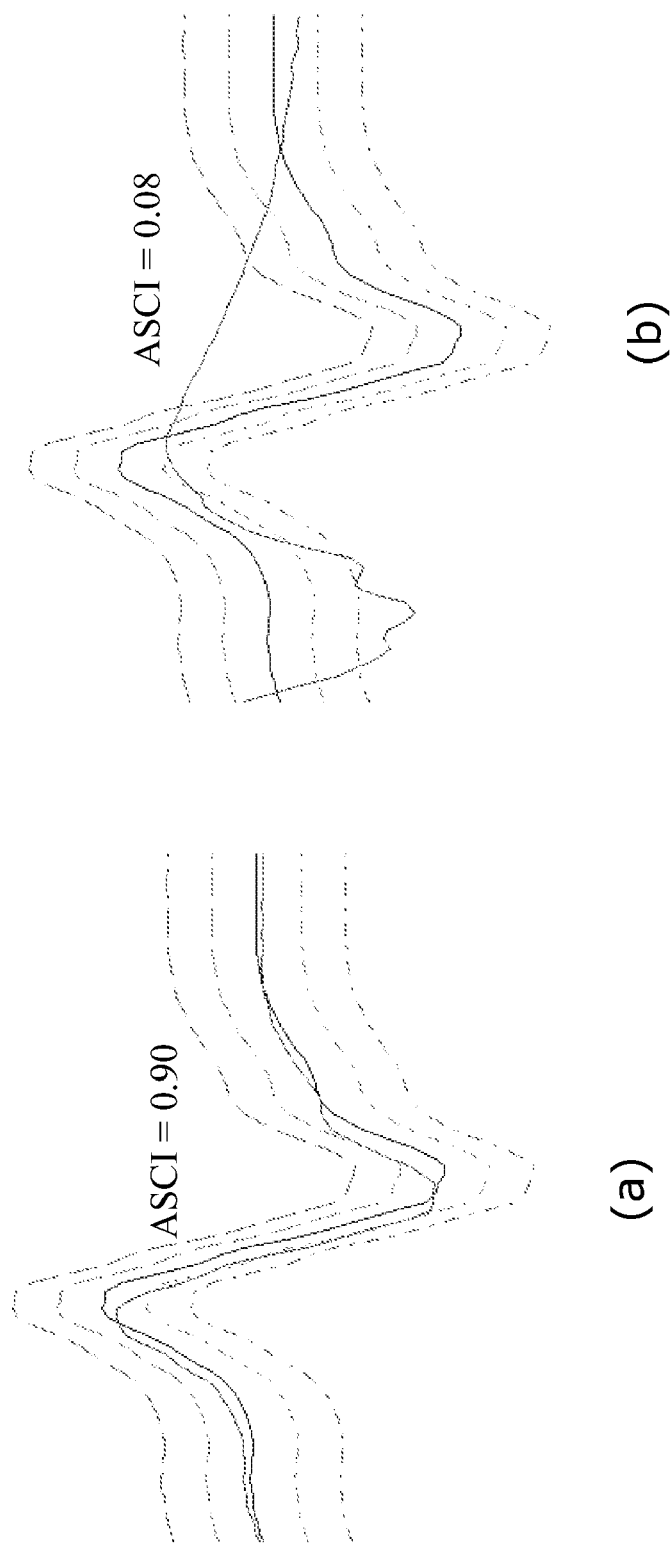
FIG. 6 shows two examples of calculating ASCI for particular application to the assessment of IEGM morphology similarity in an ICD.

Now refer to FIG. 6, which shows two examples of calculating ASCI for particular application to the assessment of IEGM morphology similarity in an ICD. In these examples, signal X (blue trace) is the template signal representing conducted ventricular IEGM. The four threshold vectors are defined based on the template signal according to the method illustrated in FIG. 5. Then the test IEGM signal Y (red trace) is trichotomized, and the corresponding ASCI(X,Y) is calculated as described above. In panel (a), the calculated ASCI(X, Y) is 0.90, whereas in panel (b), the resulting ASCI(X,Y) is 0.08. Assuming a predefined ASCI threshold of 0.50, then the supra-threshold ASCI(X,Y) obtained in panel (a) indicates X and Y have similar morphology. Contrarily, the sub-threshold ASCI(X,Y) obtained in panel (b) indicates X and Y have different morphology.

Therefore, ASCI(X,Y) provides a quantitative measure of the similarity between signals X and Y. The definition of ASCI is compatible to the conventional definition of Pearson's correlation coefficient (CC). Similar to CC, ASCI(X,Y) is a normalized index ranging from –1 to +1. If signals X and Y have similar morphology, they will have more concordant sample pairs, and ASCI(X,Y) will approach +1. On the other hand, if signals X and Y have different morphology, they will have fewer concordant sample pairs, and ASCI(X,Y) will be less. If most sample pairs of X and Y are discordant, then ASCI(X,Y) will approach −1. However, the ASCI is advantageous compared to Pearson's CC, due to at least three reasons:

First, the calculation of Pearson's CC requires extensive floating-point operation including multiplication, division, and square root. On the other hand, the calculation of ASCI only requires comparison and summation. The threshold vectors that are used to define subspaces can be automatically determined from the template signal, through simple operations such as scaling (bit shifting), adding/subtracting, thresholding, etc. The normalization operation (divided by L) can be omitted because the total number of samples (L) is a known constant. For the purpose of SVT-VT classification, the ASCI will be mainly used for comparison with predefined or user-programmable threshold to determine if two signals have similar morphology. In this case, the threshold can be defined in the form of X-out-of-Y criterion, or by means of bit shifting operation (e.g., to obtain L/2, 3L/4, 7L/8, etc.). Therefore, the calculation of ASCI is computationally much more efficient, and can be easily implemented in firmware or hardware of the ICD.

Second, Pearson's CC is a parametric measure of linear relationship, and it does not account for the amplitude difference between signals. On the other hand, the calculation of ASCI takes amplitude information into consideration. For the examples shown in FIG. 5 where the subspaces are defined by four threshold vectors which are further adaptive to the template signal X, a high ASCI(X,Y) value requires X and Y must stay close and have similar amplitude throughout the signal length (that is, Y must be bounded by proximal upper and lower threshold vectors around signal X); otherwise, low ASCI(X,Y) value is obtained.

Thirdly, Pearson's CC is affected by each sample amplitude of each signal, thus is sensitive to additive noise such as impulse noise or continuous random noise, as well as sensitive to slight yet normal signal variation. On the other hand, the ASCI(X,Y) is calculated based on trichotomized signals TX and TY, and signal trichotomization is further based on subspaces $R_P$, $R_Z$, and $R_N$ that are adaptive to the template signal. Different means to define these subspaces can provide different degrees of tolerance of signal variation. Thus a noise-free signal and the same signal added with noise could have identical trichotomized vectors. Therefore, by properly designing subspaces according to specific application and/or prior knowledge of the signal, the ASCI can be more tolerant to additive noise and normal signal variation than the Pearson's CC.

SVT-VT Classification

Because the ASCI can reliably and efficiently measure the morphological similarity between signals, it can be used to facilitate SVT and VT classification in an ICD.

Figure 7:
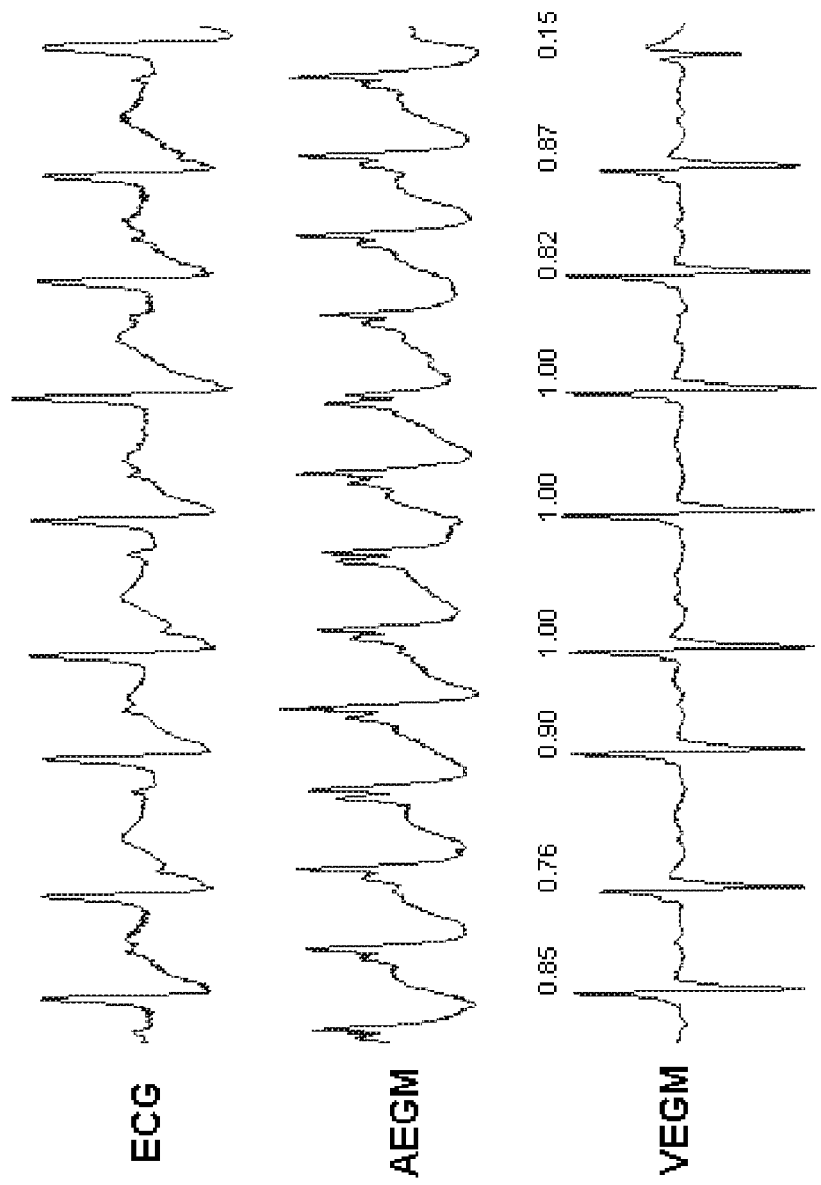
FIG. 7 shows an episode of SVT and the ASCI values between the template waveform representing conducted ventricular IEGM and each of the ventricular IEGM signal.

FIG. 7 shows an episode of SVT with 3:2 Wenckebach periodicity. In this example, the surface ECG, the atrial IEGM, and the ventricular IEGM are shown. The template waveform representing conducted ventricular IEGM was created by means of beat averaging as illustrated in FIG. 1 and FIG. 2, and the three subspaces were created by defining four threshold vectors that are adaptive to the template waveform as illustrated in FIG. 5. Then each ventricular IEGM cycle (test signal) was aligned with the template signal based on predefined fiducial point as discussed above, and the ASCI value between the test signal and the template signal was calculated. As shown in the figure, the resulting ASCI values for the first 8 ventricular cycles are high (range from 0.76 to 1.0), indicating the ventricular IEGM has similar morphology to the template signal, thus implying they are antegrade conducted beats. For the last cycle that represents a ventricular extrasystole (VES), however, the resulting ASCI value is low (0.15), indicating the ventricular IEGM has different morphology than the template signal, thus implying ventricular origin of the beat.

Figure 8:
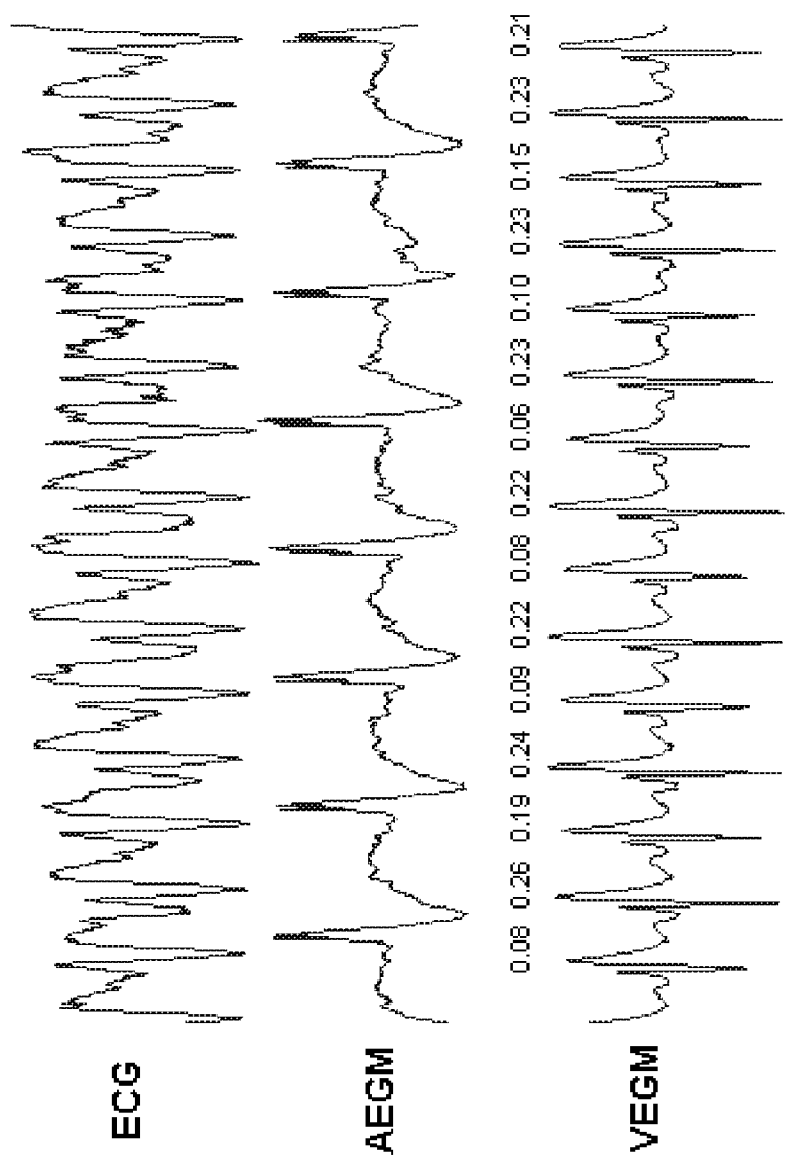
FIG. 8 shows an episode of VT and the ASCI values between the template waveform representing conducted ventricular IEGM and each of the ventricular IEGM signal.

FIG. 8 shows an episode of VT with higher ventricular rate than the atrial rate. In this example, the surface ECG, the atrial IEGM, and the ventricular IEGM are shown. Similarly, the template waveform representing conducted ventricular IEGM was created by means of beat averaging as illustrated in FIG. 1 and FIG. 2, and the three subspaces were created by defining four threshold vectors that are adaptive to the template waveform as illustrated in FIG. 5. Then each ventricular IEGM cycle (test signal) was aligned with the template signal based on predefined fiducial point as discussed above, and the ASCI value between the test signal and the template waveform was calculated. As shown in the figure, the resulting ASCI values are consistently low (range from 0.06 to 0.26), indicating the ventricular IEGM has different morphology than the template signal, thus implying ventricular origin of the beats.

In one embodiment, the SVT-VT classification is made by means of RR interval analysis combined with ASCI-based morphological analysis of the ventricular IEGM. For example, there exist VT detection algorithms which maintains an up/down VT sample counter. For single chamber devices with ventricular-only sensing, the counter is increased by each RR interval within the predefined VT/VF zone, and is decreased by each RR interval within the predefined sinus zone. A VT episode is detected if the VT sample counter exceeds a predefined threshold (e.g., 12). As known in the art, the sudden onset and RR interval stability criteria can be applied to enhance the performance of SVT-VT classification. According to this invention, such an RR interval analysis based VT detection algorithm can be further enhanced by evaluating the ASCI value between the template waveform representing conducted ventricular IEGM and each cycle of ventricular IEGM (test signal). In a preferred embodiment, a short ventricular cycle that falls in the VT/VF zone is counted toward VT (i.e., increment VT sample counter by 1) if and only if the ASCI value between the test signal and the template waveform is below a predefined threshold (e.g., 0.5). This implies that the two signals have different morphology, thus confirming ventricular origin of the ventricular beat. Otherwise, it implies that the two signals have similar morphology, thus indicating supraventricular origin of the ventricular beat. Consequently, the VT sample counter does not change or decreases by a delta value. For example, the VT sample counter does not change if $0.5 \leq ASCI < 0.7$, or is decreased by ¼ if $0.7 \leq ASCI < 0.8$, or is decreased by ½ if $0.8 \leq ASCI < 0.9$, or is decreased by 1 if $0.9 \leq ASCI \leq 1$.

In another embodiment, the ASCI-based morphological analysis is used to enhance the SVT-VT classification algorithm that involves both atrial and ventricular rate and rhythm analysis. Such algorithms analyze the average heart rate, the rate stability, and the beat-to-beat relation between atrial and ventricular activity (AV relation). Multiple detection criteria are used to determine if a short cycle (in VT zone) belongs to VT or SVT. Detailed description of detection criteria of such a SVT-VT classification algorithm is given in: Theuns et al., 'Initial clinical experience with a new arrhythmia detection algorithm in dual chamber implantable cardioverter defibrillators', Europace 2001; 3:181-186, and Sinha et al., 'Clinical experience with a new detection algorithm for differentiation of supraventricular from ventricular tachycardia in a dual-chamber defibrillator', JCE 2004; 15: 646-652.

In known SVT-VT classification algorithms, the VT sample counter is based on both RR interval and the detection decision criteria. Similarly, a VT episode is detected if the VT sample counter exceeds a predefined threshold (e.g., 12). In a typical example, the VT sample counter is increased by 1 if the RR interval is in VT zone and the cycle meets VT detection criteria. The VT sample counter is decreased by ¼ for sinus tachycardia (ST) with 1:1 AV relationship, and decreased by 1 for other SVT (e.g., atrial fibrillation, atrial flutter) interval in the VT zone. The VT sample counter is also decreased by 1 if the RR interval is in sinus interval zone. In addition, VT sample counter does not change (freeze) for a cycle in ventricular fibrillation (VF) zone. A separate counter is maintained to count the cycles in VF zone for VF detection based on conventional X-out-of-Y criterion (e.g., 8 out of 12 beats having a short RR interval in VF zone).

According to the present invention, VT detection algorithm can be further enhanced by evaluating the ASCI value between the template waveform representing conducted ventricular IEGM and each cycle of ventricular IEGM (test signal).

In an exemplary embodiment, a short ventricular cycle that meets the VT detection criteria is counted toward VT (i.e., increment VT sample counter by 1) if and only if the ASCI value between the test signal and the template waveform is below a predefined threshold (e.g., 0.5). This implies that the two signals have different morphology, thus confirming ventricular origin of the ventricular beat. Otherwise, it implies that the two signals have similar morphology, thus indicating supraventricular origin of the ventricular beat. Consequently, the VT sample counter does not change or decreases by a delta value. For example, the VT sample counter does not change if $0.5 \leq ASCI < 0.7$, or is decreased by ¼ if $0.7 \leq ASCI < 0.8$, or is decreased by ½ if $0.8 \leq ASCI < 0.9$, or is decreased by 1 if $0.9 \leq ASCI \leq 1$.

Yet in another exemplary embodiment, the ASCI-based morphology analysis is only activated to facilitate SVT-VT detection when the algorithm which is based on both atrial and ventricular rate and rhythm analysis has difficulty to determine SVT or VT rhythm, for example, when the algorithm makes the decision of SVT or VT with 1:1 AV relationship. On the contrary, when the algorithm has high confidence of its decision, for example, detection of VT when ventricular rate is higher than atrial rate, or detection of atrial fibrillation if atrial rate is higher than ventricular rate and ventricular rate is unstable, then ASCI-based morphology analysis is not needed.

According to yet another embodiment of the present invention, the ASCI-based morphology analysis is applied to atrial IEGM to facilitate SVT-VT detection when the algorithm which is based on both atrial and ventricular rate and rhythm analysis makes the decision of SVT or VT with 1:1 AV relationship. Specifically, an atrial IEGM template waveform representing intrinsic atrial depolarization is created and maintained in a similar manner as the ventricular IEGM template. When the algorithm detects SVT or VT with 1:1 AV relationship, the atrial IEGM is compared with the atrial template waveform and their ASCI value is calculated. If the resulting ASCI is higher than a predefined threshold (e.g., 0.5), then it indicates that the two signals have similar morphology. This implies the intrinsic nature of the atrial IEGM, thus the beat can be counted toward SVT. On the other hand, if the resulting ASCI is lower than the predefined threshold (e.g., 0.5), then it indicates that the two signals have different morphology. This suggests that the atrial IEGM may be the result of retrograde conduction, thus the beat can be counted toward VT.

What is claimed is:

1. A method for classifying of supraventricular tachyarrhythmia or SVT from ventricular tachyarrhythmia or VT using signals provided by an electrogram comprising:
   providing a template signal x(i) and a test signal y(i), wherein the template signal and the test signal comprise samples from an electrogram;
   defining subspaces associated with said template signal wherein R denotes a signal space that spans from $V_{min}$ to $V_{max}$, where $V_{min}$ is a minimum amplitude and $V_{max}$ is a maximum amplitude and R is divided into subspaces $R_P$, $R_Z$, and $R_N$ such that $R = R_P \cup R_Z \cup R_N$ and $R_P \cap R_Z = R_P \cap R_N = R_Z \cap R_N = \emptyset$, where $\cup$ is a union operator, $\cap$ is an intersection operator, and $\emptyset$ represents null space;
   transforming at least the test signal into a representation of the test signal ty(i) based on a trichotomization function:

$$ty(i) = \begin{cases} 1 & \text{if } y(i) \in R_P \\ 0 & \text{if } y(i) \in R_Z \\ -1 & \text{if } y(i) \in R_N \end{cases}$$

wherein ty(i) are integer values;
   determining a correlation between the template signal and the test signal by summing the representation of the test signal ty(i):

$$\sum_{i=1}^{L} ty(i)$$

wherein L represents a number of said samples; and,
   classifying of SVT from VT based on the correlation, performed using an implantable cardiac device.

2. The method according to claim 1, wherein the providing the template signal and the test signal comprises providing template and test signals from an intracardiac electrogram or IEGM, a surface electrocardiogram or ECG or a subcutaneous electrogram.

3. The method according to claim 1, wherein providing the template signal comprises obtaining the template signal by averaging a plurality of cycles of signals.

4. The method according to claim 3, wherein the averaging the plurality of cycles of signals comprises averaging a plurality of conducted ventricular IEGM signals.

5. The method according to claim 1, further comprising updating the template signal periodically or continuously.

6. The method according to claim 1, further comprising aligning the template and test signals based on at least one predefined fiducial point.

7. The method according to claim 1, further comprising:
   associating the template signal with at least two subspaces of template signal space; and,
   transforming at least one of the template signal and the test signal with respect to the at least two subspaces.

8. The method according to claim 7, further comprising defining the at least two subspaces by
   defining a first subspace comprising values which differ from template signal values at most by a predefined first value; and,
   defining a second subspace comprising values which differ from the template signal values at least by the predefined first value.

9. The method according to claim 7, further comprising associating the template signal with three subspaces and defining the three subspaces by
- defining a first subspace comprising values which differ from template signal values at most by a predefined first value;
- defining a second subspace comprising values which differ from template signal values at least by the predefined first value and at most by a predefined second value; and,
- defining a third subspace comprising values which differ from the template signal values at least by the predefined second value.

10. The method according to claim 7, further comprising bounding the at least two subspaces by threshold vectors.

11. The method according to claim 10, further comprising obtaining the threshold vectors by increasing or decreasing sample values of the template signal by a predefined value.

12. The method according to claim 1, wherein the determining the correlation comprises using transformed test signals.

13. The method according to claim 1, wherein the determining the correlation comprises using only a transformed test signal.

14. The method according to claim 1, wherein the determining the correlation comprises determining an adapted signed correlation index by summing the sample values of a transformed test signal or by dividing a sum of the sample values of the transformed test signal by a number of samples.

15. The method according to claim 1, wherein the classifying comprises classifying a ventricular IEGM as being of ventricular origin if the correlation is below a predefined threshold, or as being of supraventricular origin otherwise.

16. The method according to claim 1, wherein the classifying further comprises performing an RR interval analysis.

17. The method according to claim 16, further comprising incrementing a VT sample counter by 1 for a ventricular cycle that falls in a VT/VF zone if and only if the correlation between the test signal and the template signal is below a predefined threshold.

18. The method according to claim 1, wherein the classifying further comprises performing an SVT-VT classification algorithm that involves both atrial and ventricular rate and rhythm analysis.

19. The method according to claim 1, wherein the providing the template signal comprises providing an atrial IEGM waveform and wherein the determining the correlation further comprises distinguishing an intrinsic atrial event from a retrograde conducted atrial event when the correlation between an atrial test IEGM signal with the atrial IEGM waveform detects a 1:1 relationship between the SVT or the VT.

* * * * *

UNITED STATES PATENT AND TRADEMARK OFFICE
CERTIFICATE OF CORRECTION

PATENT NO. : 8,082,028 B2
APPLICATION NO. : 12/210381
DATED : December 20, 2011
INVENTOR(S) : Lian Page 1 of 1

It is certified that error appears in the above-identified patent and that said Letters Patent is hereby corrected as shown below:

Title Page;
In (73) Assignee: delete "Biotronix CRM Patent AG, Baar (CH)," and insert -- Biotronik CRM Patent AG, Baar (CH) --

Signed and Sealed this
Thirteenth Day of March, 2012

David J. Kappos
*Director of the United States Patent and Trademark Office*